(12) United States Patent
Topolkaraev et al.

(10) Patent No.: US 6,905,759 B2
(45) Date of Patent: Jun. 14, 2005

(54) BIODEGRADABLE FILMS HAVING ENHANCED DUCTILITY AND BREATHABILITY

(75) Inventors: Vasily A. Topolkaraev, Appleton, WI (US); Dave A. Soerens, Neenah, WI (US)

(73) Assignee: Kimberly Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/840,754

(22) Filed: Apr. 23, 2001

(65) Prior Publication Data

US 2003/0021973 A1 Jan. 30, 2003

(51) Int. Cl.[7] .............................. B32B 7/02; B32B 3/26
(52) U.S. Cl. ...................... 428/220; 428/212; 428/213; 428/216; 428/304.4
(58) Field of Search ................................ 428/220, 212, 428/213, 216, 304.4, 217; 524/17, 310

(56) References Cited

U.S. PATENT DOCUMENTS

| | | |
|---|---|---|
| 4,503,098 A | 3/1985 | Potts |
| 5,200,247 A | 4/1993 | Wu et al. |
| 5,227,415 A | 7/1993 | Masuda et al. |
| 5,336,457 A | 8/1994 | Wu et al. |
| 5,391,423 A | 2/1995 | Wnuk et al. |
| 5,412,005 A | 5/1995 | Bastioli et al. |
| 5,462,981 A | 10/1995 | Bastioli et al. |
| 5,679,421 A | 10/1997 | Brinton, Jr. |
| 5,773,562 A | 6/1998 | Gruber et al. |
| 5,786,408 A | 7/1998 | Kuroda et al. |
| 5,851,937 A | 12/1998 | Wu et al. |
| 5,879,713 A | 3/1999 | Roth et al. |
| 5,885,829 A | 3/1999 | Mooney et al. |
| 5,908,918 A | 6/1999 | Chen et al. |
| 5,916,969 A | 6/1999 | Wang et al. |
| 5,939,467 A | 8/1999 | Wnuk et al. |
| 6,075,118 A | 6/2000 | Wang et al. |
| 6,106,753 A | 8/2000 | Redd et al. |
| 6,117,438 A | 9/2000 | Topolkaraev et al. |
| 6,235,815 B1 * | 5/2001 | Loercks et al. ............... 524/47 |
| 6,432,547 B1 * | 8/2002 | Kroll et al. .............. 428/474.4 |

FOREIGN PATENT DOCUMENTS

| | | |
|---|---|---|
| JP | 8048603 A | 2/1996 |
| WO | WO90/10671 | 9/1990 |
| WO | WO 00/39211 A | 7/2000 |

\* cited by examiner

*Primary Examiner*—Rena Dye
*Assistant Examiner*—Lawrence Ferguson
(74) *Attorney, Agent, or Firm*—Brinks Hofer Gilson & Lione; G. Peter Nichols (57) ABSTRACT

The present invention is directed to biodegradable films and biodegradable precursor films having enhanced breathability and ductility. The films contain a biodegradable polymer and a water soluble polymer. The biodegradable polymer is preferably polycaprolactone, and the water soluble polymer is preferably polyethylene oxide. The precursor film of the present invention preferably has a water vapor transmission rate of at least 500 g/24 hrs/m$^2$. The biodegradable film of the present invention preferably has a water vapor transmission rate of at least 2500 g/24 hrs/m$^2$.

14 Claims, 1 Drawing Sheet

FIGURE 1

BIODEGRADABLE FILMS HAVING ENHANCED DUCTILITY AND BREATHABILITY

FIELD OF THE INVENTION

The present invention relates to highly breathable and biodegradable films that demonstrate enhanced ductility. More particularly, the present invention relates to highly breathable films and precursor films containing a biodegradable polymer and a polymer that is water soluble or water degradable.

BACKGROUND OF THE INVENTION

Disposable absorbent products currently find widespread use in many applications. For example, in the infant and child care areas, diapers and training pants have generally replaced reusable cloth absorbent articles. Other typical disposable absorbent products include feminine care products such as sanitary napkins or tampons, adult incontinence products, and health care products such as surgical drapes or wound dressings. A typical disposable absorbent product generally includes a composite structure including a topsheet, a backsheet, and an absorbent structure between the topsheet and backsheet. These products usually include some type of fastening system for fitting the product onto the wearer.

Disposable absorbent products are typically subjected to one or more liquid insults, such as of water, urine, menses, or blood, during use. As such, the outer cover backsheet materials of the disposable absorbent products are typically made of liquid-insoluble and liquid impermeable materials, such as polypropylene films, that exhibit a sufficient strength and handling capability so that the disposable absorbent product retains its integrity during use by a wearer and does not allow leakage of the liquid insulting the product.

Although current disposable baby diapers and other disposable absorbent products have been generally accepted by the public, these products still have need of improvement in specific areas. For example, the disposal of many disposable absorbent products can be difficult to accomplish. For example, attempts to flush many disposable absorbent products down a toilet into a sewage system typically lead to blockage of the toilet or pipes connecting the toilet to the sewage system. In particular, the outer cover materials typically used in the disposable absorbent products generally do not disintegrate or disperse when flushed down a toilet so that the disposable absorbent product cannot be disposed of in this way. If the outer cover materials are made very thin in order to reduce the overall bulk of the disposable absorbent product so as to reduce the likelihood of blockage of a toilet or a sewage pipe, then the outer cover material typically will not exhibit sufficient strength to prevent tearing or ripping as the outer cover material is subjected to the stresses of normal use by a wearer.

Furthermore, solid waste disposal is becoming an ever increasing concern throughout the world. As landfills continue to fill up, there has been an increased demand for material source reduction in disposable products, the incorporation of more recyclable and/or degradable components in disposable products, and the design of products that can be disposed of by means other than by incorporation into solid waste disposal facilities such as landfills.

As such, there is a need for new materials that may be used in disposable absorbent products that generally retain their integrity and strength during use, but after such use, the materials may be disposed of more efficiently. For example, the disposable absorbent product may be easily and efficiently disposed of by composting. Alternatively, the disposable absorbent product may be easily and efficiently disposed of to a liquid sewage system wherein the disposable absorbent product is capable of being degraded.

Many of the commercially available biodegradable polymers are aliphatic polyester materials. Although fibers prepared from aliphatic polyesters are known, problems have been encountered with their use. In particular, aliphatic polyester polymers are known to have a relatively slow crystallization rate as compared to, for example, polyolefin polymers, thereby often resulting in poor processability of the aliphatic polyester polymers. Most aliphatic polyester polymers also have much lower crystallization temperatures than polyolefins and are difficult to cool sufficiently following thermal processing. In addition, the use of processing additives may retard the biodegradation rate of the original material or the processing additives themselves may not be biodegradable.

Also, while degradable monocomponent fibers are known, problems have been encountered with their use. In particular, known degradable fibers typically do not have good thermal dimensional stability such that the fibers usually undergo severe heat-shrinkage due to the polymer chain relaxation during downstream heat treatment processes such as thermal bonding or lamination.

For example, although fibers prepared from poly(lactic acid) polymer are known, problems have been encountered with their use. In particular, poly(lactic acid) polymers are known to have a relatively slow crystallization rate as compared to, for example, polyolefin polymers, thereby often resulting in poor processability of the aliphatic polyester polymers. In addition, the poly(lactic acid) polymers generally do not have good thermal dimensional-stability. The poly(lactic acid) polymers usually undergo severe heat-shrinkage due to the relaxation of the polymer chain during downstream heat treatment processes, such as thermal bonding and lamination, unless an extra step such as heat setting is taken. However, such a heat setting step generally limits the use of the fiber during in situ nonwoven forming processes, such as spunbond and meltblown, where heat setting is very difficult to accomplish.

Additionally, one of the more important components of many personal care articles is the body-side liner. The liner is usually made of a surfactant-treated polyolefin spunbond. For a spunbond to be implemented as a liner, it is desired that the material be wettable to promote intake of fluid insults. In addition to rapid intake, it is desired that the composite absorbent product keep the user's skin dry. In addition, it is desirable for the spunbond material to feel soft against the skin. The current spunbond diaper liner has a number of problems. First, this diaper includes polyolefinic materials and does not degrade. Due to the hydrophobic nature of these materials, the liner must be treated with a surfactant to make it wettable. Because there is no permanent anchoring of the surfactant to the polyolefin, it has a tendency to wash off during multiple insults, increasing intake times of the nonwovens.

Furthermore, articles having a layer of a degradable polymer are relatively inflexible and do not offer a significant degree of breathability, making some articles uncomfortable to use for an extended period of time. Breathability is measured by water vapor transmission rate.

Accordingly, there is a need for an article that is biodegradable with enhanced ductility and breathability.

SUMMARY OF THE INVENTION

The present invention solves the above described problems by providing highly breathable and biodegradable films that demonstrate enhanced ductility. A breathable precursor film is described from which a biodegradable film is made. The precursor film contains a biodegradable polymer and a water soluble polymer and has a water vapor transmission rate of greater than about 500 g/m$^2$/24 hrs. Preferably the biodegradable polymer in the film is a biodegradable aliphatic polyester, and the water soluble polymer in the film is polyethylene oxide, polyethylene glycol, or a copolymer thereof.

Preferably, the precursor film contains from about 30% to about 95% by weight of the biodegradable polymer and from about 5% to about 70% by weight of the water soluble polymer. In addition, the biodegradable polymer is desirably a biodegradable resin and the water soluble polymer is a water soluble resin. The precursor film preferably has an elongation at break of greater than about 350%, and a water vapor transmission rate greater than about 1000 g/m$^2$/24 hrs. It has been demonstrated that the precursor film described herein, containing a blend of a biodegradable polymer and a water soluble polymer, exhibits enhanced breathability, ductility and softness.

The precursor film is used to produce a biodegradable film that is highly breathable and porous. The precursor film is treated by stretching, etching the water soluble resin, swelling, freeze drying, or other operations to generate the biodegradable breathable film, which has enhanced breathability and softness.

Other objects, features and advantages of this invention will become apparent upon reading the following detailed description in conjunction with the figures and claims.

DESCRIPTION OF THE PREFERRED EMBODIMENTS

The present invention is directed to highly breathable and biodegradable films having enhanced ductility to ensure softness. The films contain a biodegradable polymer and a water soluble polymer. The films include a precursor film and a biodegradable film produced from the precursor film.

The term "biodegradable" as used herein means that the film undergoes a significant change in its chemical structure under specific environmental conditions resulting in a change of properties that may vary as measured by standard test methods.

The term "breathable" as used herein means that water vapor to passes efficiently through the film.

As used herein, the term "polymer" includes homopolymers, copolymers, terpolymers and modifications thereof.

The films of the present invention are useful in the preparation of disposable personal care articles. Breathable films are commonly laminated on one or both sides of a nonwoven web, such as a spunbond web, to make a breathable laminate. A biodegradable spunbond web can serve as an effective load bearing component in a wide variety of personal care articles for which the breathable laminates are employed.

Biodegradable Polymer

Any biodegradable polymer may be used in the films. Suitable biodegradable polymers include those that are degradable in the presence of naturally occurring microorganisms so that the film loses significant strength when placed in a biologically active environment, such as a composting environment. Preferred biodegradable polymers include, but are not limited to, aliphatic polyesters such as polycaprolactone, polybutylene succinate, poly(butylene succinate-adipate), polylactic acid, a terpolymer of terephthalic acid, adipic acid and 1,4-butanediol (commercially available from BASF Corporation, Mt. Olive, N.J., under the trade name Ecoflex®); Eastar® biodegradable aliphatic polyester available from Eastman Chemical Company (Kingsport, Tenn.); and copolymers, blends and mixtures of the foregoing polymers. Preferably, the biodegradable polymer is a biodegradable aliphatic polyester. More preferably, the biodegradable polymer is a biodegradable polymer resin. Specific examples of suitable biodegradable polymer resins include the Bionolle® 1003, 3001 and 1020 resins commercially available from Showa Highpolymer (Japan), and polylactic acid resins available from Cargill Dow Polymers (Midland, Mich.).

As stated above, the biodegradable polymer is desirably a biodegradable polymer resin. The precursor film preferably contains from about 30% to about 95% by weight of the biodegradable polymer. More preferably, the precursor film contains from about 50% to about 85% by weight of the biodegradable polymer. Most preferably, the precursor film contains from about 50% to about 75% by weight of the biodegradable polymer.

Water Soluble Polymer

Any water soluble polymer may be used in the films, including but not limited to, polyethylene oxide, polyethylene glycol, polyvinyl alcohol, and copolymers and mixtures thereof. Preferably, the water soluble polymer is polyethylene oxide (PEO), polyethylene glycol (PEG), or a copolymer thereof. The water soluble polymer is more preferably a water soluble resin. The preferred PEO and PEG resins have a molecular weight from about 3,000 g/mol to about 2,000,000 g/mol. Suitable PEG resins for use in the films include CARBOWAX® resins commercially available from Union Carbide (Danbury, Conn.). Suitable PEO resins include POLYOX® resins commercially available from Union Carbide (Danbury, Conn.). Grafted or chemically modified PEO is also suitable for use in the films described herein. Suitable grafted or chemically modified PEO resins and methods of producing these resins are described in U.S. Pat. Ser. Nos. 09/001,408, 09/001,831 and 09/002,197, the disclosures of which are incorporated in their entireties herein. Other suitable commercially available water soluble polymers include ECOMATY AX-2000™ resin available from Nippon Gohsei (New York, N.Y.). Optionally, fillers, pigments, process stabilizers, and/or antioxidants may be added to the modified PEO.

As previously stated, the water soluble polymer is desirably in the form of a water soluble polymer resin. The precursor film preferably contains from about 5% to about 70% by weight water soluble polymer. More preferably, the precursor film contains from about 15% to about 50% by weight of the water soluble polymer.

Precursor Film Characteristics

The precursor film of the present invention is sufficiently stretchable to provide an elongation at break of about 350% or greater, and more preferably about 450% or greater. The precursor film is also breathable and has a water vapor transmission rate (WVTR) of at least about 500 g/m$^2$/24 hrs, preferably at least about 1000 g/m²/24 hrs, and more preferably at least about 1500 g/m²/24 hrs using a standard analysis method such as a Mocon® high permeability test method. Most preferably, the precursor film has a water vapor transmission rate of at least 2000 g/m²/24 hrs.

Preferably, the precursor film has a thickness of less than about 5 mils. More preferably, the precursor film has a thickness of less than about 2 mils, and most preferably less than about 1 mil.

The inclusion of a water soluble polymer provides the precursor film with the characteristic of enhanced wettability.

Biodegradable Film

A biodegradable film made from a precursor film is also provided herein. The water soluble polymer in the biodegradable film is preferably in a concentration between about 1% and about 50% by weight of the film. Preferably, the water soluble polymer is present in a concentration between about 5% and about 30%. The biodegradable polymer in the film is preferably in a concentration between about 50% and about 99% by weight of the film. More preferably, the biodegradable polymer is present in a concentration between about 70% and about 95%. In addition, the water soluble polymer is preferably in the form of a water soluble polymer resin, and the biodegradable polymer is preferably in the form of a biodegradable polymer resin.

The biodegradable film is highly breathable and porous, and has a water vapor transmission rate of greater than about 2500 g/m²/24 hrs. Preferably, the biodegradable film has a water vapor transmission rate of greater than about 3000 g/m²/24 hrs, more preferably greater than about 3500 g/m²/24 hrs.

In addition, the biodegradable film has enhanced ductility and an elongation at break of at least 100%. Desirably, the biodegradable film has an elongation at break of at least 200%.

Preferably, the biodegradable film has a thickness from about 0.01 to about 5 mils. More preferably, the biodegradable film of the present invention has a thickness from about 0.01 to about 2 mils.

The biodegradable film is especially suitable for use in personal care products. This film has a high water vapor transmission rate and breathability to prevent the accumulation of perspiration in personal care products, thereby increasing the comfort level experienced by the product user. Furthermore, the biodegradable film has sufficient ductility, flexibility and strength to be processed by standard processing methods and equipment used in the production of personal care products. The biodegradable film is particularly useful in disposable personal care products such as diapers, training pants, feminine pads, panty liners, incontinence products, as well as personal health products such as wound dressings, and delivery systems.

Film Production

Figure 1:
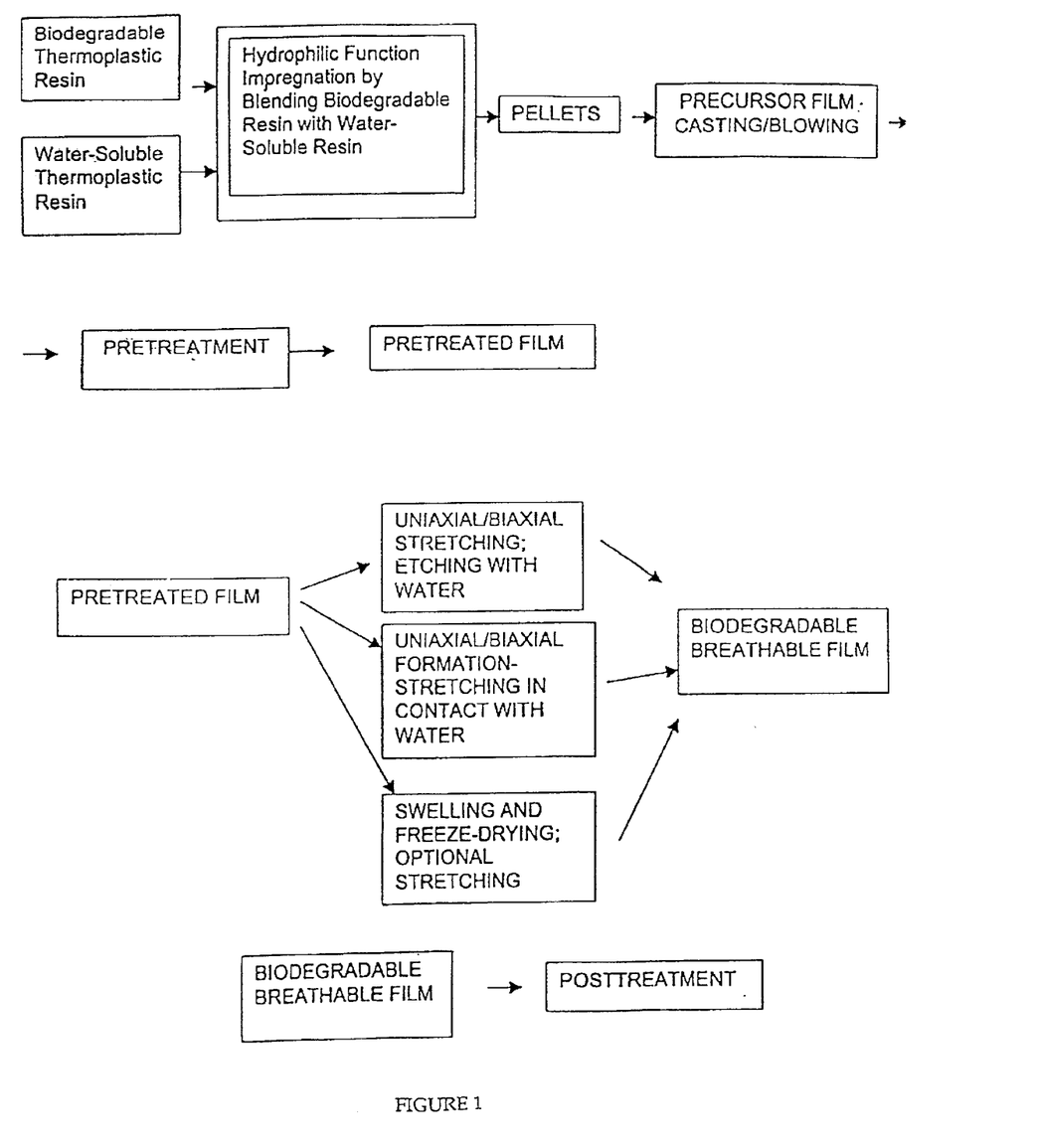
FIG. 1 is a block diagram illustrating the methodology of the present invention.

As mentioned above, the biodegradable film is produced by processing the precursor film described herein and shown in FIG. 1. The precursor film is produced as follows. The water soluble polymer and biodegradable polymer, both described above, are blended to form a blended polymer mixture. The mixture may also include additional components such as fillers. The water soluble polymer, biodegradable polymer and additional components may be blended by any method known in the art. For example, melt mixers, blenders, single extruders and multi-screw extruders may be used. Twin-screw extruders are the preferred blending device since excellent distributive and dispersive mixing are provided using this type of extruder. Additionally, counter-rotating and co-rotating twin screw extruders may also be used to blend the polymers. One example of a suitable blending device is a ZSK-30 twin screw extruder manufactured by Werner & Pfleiderer (Tamm, Germany).

The selection of a filler material to be used in forming the precursor film is based on a consideration of key parameters such as particle size, expansion and swelling efficiency, and interaction with the polymer. To prevent critical flaw formation during stretching, filler size should be, on average, 1 micron with a top cut desirably below 10 microns. Particles greater than 10 microns may result in excessive discontinuity during stretching and stress build-up in the polymer. Likewise, very fine particles of less than 0.2 microns are also not desirable during material processing because of agglomeration and increased reinforcing properties. Thus, fillers with small aspect ratios and low coupling with the blended polymer resin are desired.

Suitable filler materials are organic or inorganic, and are desirably in a form of individual, discreet particles. Desirably, the average particle size of the filler material does not exceed about 10 microns, more desirably does not exceed 8 microns, even more desirably does not exceed about 5 microns, and preferably does not exceed about 1 micron. Suitable inorganic filler materials include metal oxides, metal hydroxides, metal carbonates, metal sulfates, various kinds of clay, silica, alumina, powdered metals, glass microspheres, or vugular void-containing particles. Particularly suitable filler materials include calcium carbonate, barium sulfate, sodium carbonate, magnesium carbonate, magnesium sulfate, barium carbonate, kaolin, carbon, calcium oxide, magnesium oxide, aluminum hydroxide, and titanium dioxide. Still other inorganic fillers can include those with particles having higher aspect ratios such as talc, mica and wollastonite. Suitable organic filler materials include for example, latex particles, particles of thermoplastic elastomers, pulp powders, wood powders, cellulose derivatives, chitin, chitosan powder, powders of highly crystalline, high melting polymers, beads of highly crosslinked polymers, organosilicone powders, and powders of superabsorbent polymers, such as partially neutralized polyacrylic acid, and the like, as well as combinations and derivatives thereof. These filler materials can improve toughness, softness, opacity, vapor transport rate (breathability), water dispersability, biodegradability, fluid immobilization and absorption, skin wellness, and other beneficial attributes of the film.

Suitable commercially available filler materials include the following:

1. SUPERMITE®, an ultrafine ground $CaCO_3$, which is available from ECC International of Atlanta, Ga. This material has a top cut particle size of about 8 microns and a mean particle size of about 1 micron.

2. SUPERCOAT®, a coated ultrafine ground $CaCO_3$, which is available from ECC International of Atlanta, Ga. This material has a top cut particle size of about 8 microns and a mean particle size of about 1 micron.

3. OMYACARB® UF, high purity, ultrafine, wet ground $CaCO_3$, which is available from OMYA, Inc. of Proctor, Vt. This material has a top cut particle size of about 4 microns and an average particle size of about 0.7 microns and provides good processability.

4. OMYACARB® UFT $CaCO_3$, an ultrafine pigment surface coated with stearic acid, available from OMYA, Inc. This material has a top cut particle size of about 4 microns and a mean particle size of about 0.7 microns and provides good processability.

Sometimes it is desirable to modify the surface of the filler with a surface modifying agent to improve the surface properties of the fillers or the resulting films. The filler can be coated with liquid additives to reduce coupling at the resin-filler interface. Decoupling should facilitate debonding of filler from polymer matrix during stretching. This is especially important for the polar biodegradable aliphatic polyester, which demonstrates strong interaction with fillers. At the same time, the coating should provide affinity to polymer resin for improved dispersion and deagglomeration. Examples of such additives include silicone glycol copolymers of different Hydrophilic-Lipophilic Balance (hereinafter HLB) numbers ranging from 0 to about 12. Such silicone glycol copolymers are available from Dow Corning Corporation. The variation in HLB number can provide controlled interaction of the coated filler with the biodegradable resin and the water soluble resin. More specifically, FF-400 additive (HLB=6.6) and 193 surfactant (HLB=12) have been used to coat calcium carbonate in a solvent-surfactant solution. Filler also can be precompounded with a surfactant before mixing with the resin, or additive can be compounded with the resin and filler at the melt-blending step. The later method reduces the effectiveness of the coating.

The precursor film produced from the polymer/filler mixture preferably contains from about 10 percent to about 70 percent by weight of the filler. More preferably, the precursor film contains from about 20 percent to about 50 percent by weight of the filler.

In addition to the biodegradable polymer, water soluble polymer and the filler, the precursor film, finished biodegradable film and articles produced in the present invention may optionally contain various additives such as plasticizers, processing aids, rheology modifiers, antioxidants, UV light stabilizers, pigments, colorants, slip additives, antiblock agents, etc. which may be added before or after blending with the filler.

In addition, inorganic fillers may include water soluble fillers including, but not limited to, magnesium sulfate, sodium sulfite, sodium hydrogen sulfite, sodium sulfate, sodium hydrogen sulfate, sodium phosphate, sodium hydrogen phosphate, sodium carbonate, sodium hydrogen carbonate, potassium carbonate, sodium hydroxide, potassium hydroxide, sodium chloride, and, where applicable, hydrates thereof.

Plasticizers can improve processability of the precursor film described herein, enhance draw ratio during stretching operations and reduce modulus, yield stress, and stress required for stretching the film. Plasticization can enhance the processability of various biodegradable polyester polymers including, but not limited to polylactic acid, which typically demonstrates very large tensile modulus around 2000 Mpa and very low elongation at break of around 3%. Plasticization of biodegradable polymers can dramatically enhance elongation at break and reduce modulus of the film.

Suitable plasticizers for polylactic acid (PLA) and other biodegradable polymers include, but are not limited to polyethylene glycol of varying molecular weight from about 500 g/mol to about 20,000 g/mol, phthalic acid derivatives such as dimethyl phthalate, diethyl phthalate and butyl benzyl phthalate, citric acid derivatives such as tri-n-butyl citrate and tri-n-butyl acetylcitrate, benzoic acid derivatives such as diethylene glycol dibenzoate, sebacic acid derivatives such as dibutil sebacate and dioctyl sebacate, glycerol esters such as glycerol triacetate and glycerol tripropionate. Various polymeric plasticizers such as adipate derivatives are also suitable. Different plasticizers can be combined or mixed together before or during compounding with the PLA or other biodegradable polyester polymers to improve and enhance the plasticization effect, and reduce migration and phase separation of the plasticizer during aging of the film. For example, polyethylene glycol can be combined with a phthalic acid derivative such as dimethyl phthalate, and the mixture can be blended with polylactic acid. Other combinations of different plasticizers including citric acid derivatives, glycerol esters and phthalic acid derivatives might also be useful. Different plasticizers can also be fed separately into an extruder during the compounding step and preparation of the precursor film.

The overall amount of plasticizer or combination of plasticizers can be in the range of 5 to 40 percent by weight, and more preferably from 10 to 30 percent by weight of the biodegradable polymer.

After the blended polymer mixture containing optional fillers and additives has been produced, it is then formed into the precursor film using a variety of techniques, including but not limited to, casting, blowing, or compression molding as shown in FIG. 1. For example, a twin screw extruder may be used to form the precursor film, however, any method know in the art may be utilized. A chilled wind-up roll may optionally be used to collect the precursor film from the extruder.

The precursor film is then processed to produce a biodegradable film that has the desired characteristics of porosity, breathability, and ductility. Preferred methods of processing the precursor film are shown in FIG. 1. This process may include stretching the precursor film. Stretching allows the films of the present invention to have a desired breathability and/or thickness. If desired, the precursor film can be pretreated to prepare the film for the subsequent stretching operation. The pretreatment can be performed by annealing the resulting precursor film at elevated temperatures or by spraying the precursor film with a surface active liquid, such as water or other aqueous solution. Additional pretreatments include modifying the physical state of the polymer in the film through the use of ultraviolet radiation, an ultrasonic treatment, high-energy irradiation, microwave treatment, and/or other non-direct contact treatment. In addition, the pretreatment may incorporate a combination of two or more of the foregoing techniques.

Any uniaxial or biaxial stretching machine known in the art may be used to perform the stretching operation. The precursor film may be subjected to a plurality of stretching operations, such as uniaxial stretching or biaxial stretching to specified draw ratio. Stretching operations can provide a porous film with distinctive porous morphology, can enhance water vapor transport through the film, and can improve water access, and enhance degradability of the film. Preferably, the film is stretched from about 100 to about 500 percent of its original length. More preferably, the film is stretched from about 100 to about 300 percent of its original length.

The key parameters during stretching operations include stretching draw ratio, stretching strain rate, and stretching temperature. In one particular aspect of the invention, the draw or stretching system may be constructed and arranged to generate a draw ratio which is not less than about 2.0 in the machine and/or transverse directions. The draw ratio is the ratio determined by dividing the final stretched length of the film by the original unstretched length of the film along the direction of stretching. Preferably, the draw ratio in the machine direction (MD) is not less than about 2.0 and more preferably is not less than about 3.0. In another aspect, the stretching draw ratio in the MD is preferably not more than about 8. More preferably, the draw ratio is not more than about 6.

The factors used to determine the amount of stretching may include, but are not limited to, the desired water vapor transmission rate for the film and the desired thickness of the final film. Through the process of stretching, it is possible to create composite films having a water vapor transmission rate of at least about 2500 g/m²/24 hours.

The precursor film can also be prewetted before the stretching. However, in the preferred method, the precursor film is stretched while in contact with a solvent. Suitable solvents include but are not limited to water, methanol, ethanol and any solvents known in the art which are capable of dissolving the water soluble component of the film. It has been demonstrated that water acts as a surface-active media during film stretching. The contact with water during the stretching process can reduce the surface energy between the film material and environment, which can lower the stress required to produce a stretched film with a specified draw ratio. It can also reduce the probability of a film failure during the stretching process as the precursor film will be experiencing lower stresses during stretching. In addition, stretching in contact with water can accelerate the dissolution and etching of the water soluble component of the film by plastically deforming the water soluble component while it is in contact with the solvent Furthermore, stretching in contact with a solvent increases the breathability of the film, improves its softness and reduces film thickness.

Additionally, the thickness of the precursor film may be modified by stretching. Preferably, precursor film has a thickness of less than about 5 mils. More preferably, precursor film has a thickness of less than about 2 mils. When the precursor film is stretched while in contact with a solvent, precursor films having a thickness of less than about 1.0 mil are possible while still retaining enhanced breathability, ductility and biodegradability of the film.

After stretching, the water soluble polymer may be etched or dissolved by water for a desired time interval, preferably not less than one minute. The stretching procedure and etching of the water soluble component of the precursor film can be accomplished in separate steps with the etching step following or preceding the stretching procedure.

In one embodiment of the present invention, the precursor film is freeze-dried to modify the morphology of the film. The freeze-drying operation includes immersing the film in a solvent to swell the film. Next, the precursor film is immediately immersed in liquid nitrogen. Suitable solvents include but are not limited to water, methanol, ethanol and any solvents known in the art which are capable of dissolving the water soluble component of the film. Typically the solvent is water. The precursor film may be transferred to a pre-cooled freeze-dryer and kept under vacuum for approximately two hours. The film is then returned to room temperature, preferably under vacuum. The freeze-dried film can be optionally stretched to further modify the morphology of the film or the freeze-drying operation can be performed alone.

In a swelling and freeze drying operation, for efficient moisture penetration into the film structure, the precursor film should contain at least about 30% by weight of a water soluble component. The swelling and freeze-drying procedure produces a highly porous film with dramatically enhanced water vapor permeability as a result of a high void content. The swelling process can also be accomplished in combination with the film stretching.

The precursor film processed according to any of the methods set forth above may then be delivered to a post-treatment device to produce the final biodegradable film. The post-treatment device may provide drying to remove solvent or water, a heat-setting and/or annealing operation. During the post-treatment operation, the film may be held under tension at elevated temperatures. Additional post-treatment processes or operations such as ultraviolet treatment, ultrasonic treatment, microwave or RF wave treatment can be incorporated to modify the morphological state of the final biodegradable film or reduce the moisture content in the film.

The biodegradable film formed according to the method described herein exhibits enhanced ductility, softness and breathability. The biodegradable film can then be advantageously used in the preparation of a wide variety of products including various disposable personal care products and health care products.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Preparation of Polyethylene Oxide Resins

In this example, the following unmodified and modified polyethylene oxide (PEO) resins were used: 1) A grafted PEO 205 resin was produced using batches containing 98.7% by weight WSR-205 Polyox® powder resin supplied by Union Carbide Corporation (molecular weight of 600,000 g/mol), 1.3% by weight $TiO_2$ pigment, a stabilizer package including 1000 ppm Irganox® 1010, 1000 ppm Irganox® 1076, and 2000 ppm Irgafos® 168. The dry blended powder batches were then reactively extruded with 1.5% by weight of 2-hydroxethyl methacrylate (HEMA) and 0.15% by weight peroxide, Lupersol 101, using a ZSK-30 twin screw extruder (manufactured by Werner & Pfleiderer) at a rate of 20 lbs/hr. The resulting extrudant was then pelletized. 2) A grafted PEO N80 resin was produced using Polyox® WSR-N80 powder resin from Union Carbide Corporation. The resin was extruded using the ZSK-30 twin screw extruder operated at a rate of 20 lbs/hr. Polyethylene glycol methacrylate (PEG-MA) of 246 g/mol molecular weight was injected at a rate of 5% or 1 lb/hr and a peroxide Lupersol 101 was injected at a rate of 0.4% or 0.008 lb/hr during the reactive extrusion process. The resulting extrudant was then pelletized. 3) Polyox® WSR-N80 powder resin from Union Carbide Corporation with a reported molecular weight of 200,000 g/mol was pelletized at Planet Polymer Technologies of San Diego, Calif.

Example 2

Polyethylene Oxide/Bionolle 3001 Polymer Blend Preparation

The water soluble resin of Example 1 and a Bionolle® 3001 biodegradable aliphatic polyester resin were fed into a ZSK-30 twin screw extruder at a rate of 20 lb/hr. The extruder temperatures were set at 170, 180, 180, 180, 180, 180, and 170° C. for zones 1 through 7 on the extruder. Blends comprising the following weight percent ratios based on total weight of the blend were produced: 15/85 grafted PEO N80/Bionolle® 3001, 25/75 grafted PEO N80/Bionolle® 3001, 50/50 grafted PEO N80/Bionolle® 3001, 15/85 grafted PEO 205/Bionolle® 3001, 25/75 grafted PEO 205/Bionolle® 3001, 50/50 grafted PEO 205/Bionolle® 3001.

Example 3
Polyethylene Oxide/Bionolle 3001 Precursor Film Preparation

Precursor films were produced from the blended resins of Example 2 using a Haake twin screw extruder assembled with a melt pump and 4" film die. Enhanced wettability was imparted into the precursor films by blending with the water-soluble resin (see FIG. 1). During film processing, the screw speed was held constant at 21 rpm. The melt pump speed was adjusted to accommodate the different flow properties of the resins. A chilled wind-up roll that was maintained at 15 to 20° C. was used to collect the film. Films with a targeted thickness of about 1 mil to about 2 mil were collected from each resin. The film tensile properties and water vapor transport rate were analyzed.

Tensile Properties and Breathability of the Polyethylene Oxide/Bionolle 3001 Precursor Films Tensile properties of the precursor films made from blends of Bionolle 3001 resin and grafted PEO are illustrated in Tables 1 and 2. The tensile properties were determined by ASTM D683-91 using a dog-bone specimen configuration, two inch gauge length, and five inch per minute crosshead speed. The blends with both grafted PEO 205 and grafted PEO N80 showed significantly improved elongation at break from about 500% up to 850% compared to a control Bionolle 3001 resin with elongation at break of 363%. At 15 weight percent of grafted PEO resin loading, tensile modulus was lower compared to a control resin. Specifically the tensile modulus was 90 Mpa to 120 Mpa, compared to 160 Mpa. In addition, for grafted PEO N80 resin a reduction in yield stress was observed. All these changes in film ductility and stiffness are desired for the stretch post processing of the film.

Breathability of the precursor films is illustrated in Table 3. An unexpected dramatic increase of breathability was observed with the addition of grafted PEO resin. With only 15 weight percent PEO, the breathability of the precursor film increased from about 850 g/m$^2$/24 hrs for the control film up to about 2000 g/m$^2$/24 hrs. A synergistic interaction of a biodegradable resin and a water soluble resin produced a significant increase in breathability.

The breathability, or water vapor transport rate was measured in accordance with ASTM F-1249 by using the Permatran 100K analyzer available from Mocong Testing Services (Minneapolis, Minn.). The test conditions were: temperature of 37.0° C., relative humidity of 100% on one side of the film and 0% on the other side.

TABLE 1

Tensile Properties in Machine Direction of Polyethylene Oxide/Bionolle 3001 Precursor Films

| Blends | Thickness (mil) | Peak Stress (MPa) | Break Stress (MPa) | Elongation @ Break (inch) | % Strain@ Break |
|---|---|---|---|---|---|
| grafted PEO N80/Bionolle 3001 | | | | | |
| 15/85 | 1.34 | 23 | 22 | | 509 |
| 50/50 | 1.50 | 15 | 14 | | 579 |
| grafted PEO 205/Bionolle 3001 | | | | | |
| 15/85 | 1.36 | 25 | 24 | | 613 |

| Blends | Thickness (mil) | Peak Load (g) | Break Stress (MPa) | Elongation @ Break (inch) | % Strain@ Break |
|---|---|---|---|---|---|
| 50/50 | 1.07 | 284 | 32 | 6 | 847 |
| 25/75 | 2.0 | 543 | 32 | 5 | 655 |
| Polybutylene Succinate adipate Copolymer, Bionolle 3001 | | | 40 | | 363 |

TABLE 2

Tensile Properties in Machine Direction of Polyethylene Oxide/Bionolle 3001 Precursor Films

| Blends | % Strain @ Yield | Yield Stress (MPa) | Modulus (MPa) | Tensile Energy @ Break (Joule/cm$^3$) |
|---|---|---|---|---|
| grafted PEO N80/Bionolle 3001 | | | | |
| 15/85 | 74 | 11 | 87 | 88 |
| 50/50 | 12 | 8 | 167 | 84 |
| grafted PEO 205/Bionelle 3001 | | | | |
| 15/85 | 16 | 9.6 | 118 | 108 |
| 50/50 | | 15 | 212 | 185 |
| 25/75 | | 14 | 161 | 150 |
| Polybutylene Succinate adipate Copolymer, Bionolle 3001 | | 15 | 156 | |

TABLE 3

Breathability of Polyethylene Oxide/Bionolle 3001 Precursor Films

| BLENDS | FILM THICKNESS | BREATHABILITY g/m²/24 hrs |
|---|---|---|
| 15/85 grafted PEO N80/Bionolle 3001 | 1.2 mil | 1860 |
| 15/85 grafted PEO 205/Bionolle 3001 | 1.2 mil | 2160 |
| CONTROL Bionolle 3001 | 1 mil | 850 |

Example 4

Polyethylene Oxide/Bionolle 3001 Precursor Film Stretching in Contact with a Solvent The precursor films produced as described in Example 3 were stretched in machine direction to a specified draw ratio in contact with water. The draw ratios were in the range from 2 to 3.5. After stretching, the water soluble resin was etched by water for about 1 minute. The stretched film samples were then dried in a convection oven for about 12 hrs at 40° C.

Example 5

Freeze-Drying of Swelled Polyethylene Oxide/Bionolle 3001 Precursor Film

Swelling and freeze drying operations were demonstrated to significantly modify the morphology of the film described in Example 4. The precursor film was immersed into deionized water for about 30 seconds to about 2 minutes. Next, the film was immediately immersed in a liquid nitrogen bath. The film in a frozen state, was transferred into a pre-cooled freeze-dryer and was kept under vacuum at −39° C. for 2 hrs to remove all ice. After freeze-drying, the film was returned under vacuum to room temperature. The structure of the film was analyzed using scanning electron microscopy techniques.

Example 6

A precursor film cast from a (70/30) PEO N80/Bionolle® 1020 blend, as described in the examples above, was swelled in deionized water for 2 minutes and freeze-dried. The cross-sectional morphology of the film was analyzed using SEM. A unique, fine cellular structure formed by interconnected network of polymeric fibrils was demonstrated. The high void content and interconnected void morphology of the film provides a dramatic increase in water vapor permeability of the film.

Example 7

Breathability of the Stretched Polyethylene Oxide/Bionolle 3001 Precursor Films

The precursor films described in Example 3 were stretched in machine direction in contact with water. The films were etched with water for an additional 1 minute after stretching was complete and then dried at 40° C. for 12 hrs. The breathability of the stretched dried films were measured using MOCON® Permatran 100K analyzer at 37° C. SEM technique was used to analyze the morphology of the films.

The precursor film made from a 15/85 grafted PEO 205/Bionolle® 3001 blend was stretched 2.9× in MD in contact with water. The stretched film thickness after drying was about 0.7 mil. The film breathability was measured to be about 3100 g/m²/24 hrs. The estimated weight loss after PEO etching was about 8%. The SEM analysis of the film surface showed a textured surface with fine voids, with longer axes oriented perpendicular to the stretch direction. Void size was about 0.1 micron.

The precursor film made from a 25/75 grafted PEO 205/Bionolle® 3001 blend was stretched 2.6× in MD in contact with water. The stretched film thickness after drying was about 1.2 mil. The film breathability was measured to be about 2600 g/m²/24 hrs. The estimated weight loss after PEO etching was about 7%. The SEM analysis of the film surface showed a highly textured surface oriented in MD direction. Randomly distributed voids were embedded in the textured surface of the film.

The precursor film made from a 50/50 grafted PEO 205/Bionolle® 3001 blend was stretched 3.0× in MD in contact with water. The stretched film thickness after drying was about 1.0 mil. The film breathability was measured to be about 3800 g/m²/24 hrs. The estimated weight loss after PEO etching was about 24%. The SEM analysis of the film surface showed a highly textured surface with orientation in both MD and CD directions. Very fine micro domain morphology of the film surface indicated an efficient etching of the PEO phase.

The precursor film made from a 25/75 grafted PEO 205/Bionolle® 3001 blend was stretched 2.5× in MD in contact with water. The stretched film thickness after drying was about 0.65 mil. The film breathability was measured to be about 3500 g/m²/24 hrs.

The obtained results indicate that the breathability of the biodegradable precursor film made from a blend of biodegradable and water soluble resins can be significantly enhanced by stretching the film while in contact with water. Film thinning and an efficient etching of a water soluble phase can be responsible for the observed improvement in breathability. Compared to plain Bionolle® resin, an improvement in breathability in the range of four times was demonstrated.

Example 8

Preparation of Polylactic Acid Polymer Blend

The film grade biodegradable aliphatic polyester polylactic acid (PLA), which was obtained from Cargill Dow Polymers LLC, was blended with polyethylene glycols (Carbowax® PEG) of various molecular weights (PEG 8000, MW=8000g/mol and PEG 3400, MW=3400 g/mol) and polyethylene oxide (PEO) Polyox® WSR N-10 resin having a molecular weight of about 100,000g/mol. Both PEG and PEO water soluble resins were obtained from Union Carbide Corporation. The blends were compounded using a ZSK-30 twin screw extruder. The extruder temperatures were set at 170° C., 180° C., 190° C., 190° C. 190° C., 180° C., 170° C. for the zones 1 through 7 on the extruder. The produced blends had a concentration of water soluble resins varying from about 5% by weight of the total blend weight up to 30% by weight of the total blend weight. The PLA resin was dried at 85° C. overnight prior to compounding.

The PLA/PEO blends of 85/15 and 70/30 composition were also compounded with calcium carbonate (CaCO₃) filler at 45 weight percent loading relative to the blend composition. The filler was obtained from ECC International, of Sylacauga, Ala., and had an average particle size of about 1 micron.

Example 9

Polylactic Acid Blend Precursor Films

Precursor films were produced from the blended resins of Example 8 using a Haake twin screw extruder assembled with a melt pump and 8" film die. The melt pump speed was adjusted to accommodate the different flow properties of the resins. The chilled wind-up roll was used to collect the film. Films with targeted thickness of about 1 mil to about 2 mil were collected. The film tensile properties and water vapor transmission rate were analyzed.

Example 10
Tensile Properties and Breathability of the PLA Blend Precursor Films Tensile properties of the precursor films produced in Example 8 were measured in machine direction at room temperature except for the blends with calcium carbonate filler. The filled blends were tested at 55° C. to enhance the stretchability of the films. Typically the tensile tests of the films were done in 2–3 hours after film casting. It was observed that the films could change the tensile properties as a result of aging and migration, and crystallization of the water soluble resin. The tensile modulus of the films can increase and strain at break can drop as a result of a film aging even at ambient environment. Preferably, stretching operations are conducted immediately after the films are cast.

The properties of the PLA based precursor films are illustrated in Table 4. As can be seen in Table 4, blending of the PLA resin with water soluble resins can provide precursor films with dramatically enhanced percent strain at break compared to the plain PLA resin. The percent strain at break was increased from about 3% for control PLA film to 200%–400% range for the blends with water soluble resins. Tensile modulus of the blend films as well as yield stress was dramatically reduced compared to the PLA control film. These changes in tensile properties are beneficial for stretching operations. A precursor film having a higher strain at break can provide larger draw ratios during post stretch processing, while lower modulus and yield stress can reduce stress applied to the precursor film during stretching. Higher content of water soluble resins in the blend, for example above 15 weight percent was more beneficial for the desired change in tensile properties. Aging of the PLA/water soluble resin blend films can result in undesirable deterioration of the tensile properties of the films. Breathability of the precursor film was also improved from 200 g/m$^2$/24 hrs for the PLA film to about 520 g/m$^2$/24 hrs for the PLA/PEG 8000 70/30 precursor film.

TABLE 4

Tensile Properties and Breathability of Polylactic Acid Blend Precursor Films

| Blends | Thickness (Mil) | Break Stress (Mpa) | % Strain@Break | Yield Stress (Mpa) | Modulus (Mpa) | Breathability g/m$^2$/24 hrs |
|---|---|---|---|---|---|---|
| 70/30 PLA/PEG 8000 | 1 | 28 | 320 | 12 | 270 | 520 |
| 75/25 PLA/PEG 8000 | 1.9 | 39 | 385 | 8 | 143 | |
| 80/20 PLA/PEG 8000 | 1.6 | 48 | 410 | 16 | 468 | |
| 95/5 PLA/PEG 8000 | 0.9 | 42 | 13 | 54 | 2160 | |
| 80/20 PLA/PEG 3400 | 1.08 | 36 | 40 | 53 | 1968 | |
| 85/15 PLA/PEO + 45 wt. % CaCO$_3$ Filler Test @ 55° C. | 0.96 | 13 | 350 | | | |
| 70/30 PLA/PEO + 45 wt % CaCO$_3$ Filler Test @ 55° C. | 0.96 | 8 | 230 | 4 | 43 | |
| 85/15 PLA/PEO | 0.91 | 29 | 124 | 42 | 648 | |
| 70/30 PLA/PEO | 0.78 | 42 | 210 | 11 | 172 | |
| 80/20 PLA/PEO (PEO MW = 100,000) | 1.1 | 34 | 230 | 29 | 946 | |
| CONTROL Polylactic Acid | 1.85 | 65 | 3.3 | 65 | 2118 | 200 |

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. A biodegradable stretched film comprising:

a biodegradable polymer; and a water soluble polymer, wherein the film has a thickness from about 0.01 to about 5 mils, is breathable and further wherein the film is porous and wettable and is stretched from about 100 to about 500 percent of an original length to provide a water vapor transmission rate greater than about 2500 g/m$^2$/24 hrs and an elongation at break of greater than about 100%.

2. The film of claim 1, wherein the biodegradable polymer is an aliphatic polyester.

3. The film of claim 1, wherein the biodegradable polymer is selected from the group consisting of polycaprolactone, polybutylene succinate, poly(butylene succinate-adipate), polylactic acid, terpolymers of terephthalic acid, adipic acid, and 1,4-butanediol, and copolymers and mixtures thereof.

4. The film of claim 1, wherein the water soluble polymer is selected from the group consisting of polyethylene oxide, polyethylene glycol, polyvinyl alcohol, and copolymers and mixtures thereof.

5. The film of claim 1, wherein the water soluble polymer is polyethylene oxide, polyethylene glycol or a copolymer thereof.

6. The film of claim 1, wherein the biodegradable polymer is polycaprolactone and the water soluble polymer is polyethylene oxide.

7. The film of claim 1 having a water vapor transmission rate of greater than about 3000 g/m$^2$/24 hrs.

8. The film of claim 1 having a water vapor transmission rate of greater than about 3500 g/m$^2$/24 hrs.

9. The film of claim 1 having an elongation at break of greater than about 200%.

10. The film of claim 1, wherein the film includes from about 1% to about 50% water soluble polymer by weight of the film.

11. The film of claim 1, wherein the film includes from about 5% to about 30% water soluble polymer by weight of the film.

12. The film of claim 1, wherein the film includes from about 50% to about 99% biodegradable polymer by weight of the film.

13. The film of claim 1, wherein the film includes from about 70% to about 95% biodegradable polymer by weight of the film.

14. The film of claim 1 having a thickness of from about 0.01 to about 2 mils.

* * * * *